United States Patent [19]

Roy

[11] Patent Number: 4,542,748

[45] Date of Patent: Sep. 24, 1985

[54] APPARATUS AND METHOD FOR MEASURING CARDIAC OUTPUT

[75] Inventor: Rob J. Roy, Clifton Park, N.Y.

[73] Assignee: American Hospital Supply Corp., Evanston, Ill.

[21] Appl. No.: 472,931

[22] Filed: Mar. 7, 1983

[51] Int. Cl.[4] .............................................. A61B 5/02
[52] U.S. Cl. ..................................... 128/713; 128/736
[58] Field of Search ........................ 128/692, 713, 736

[56] References Cited

U.S. PATENT DOCUMENTS 3,620,207  11/1971  Sinclair ............................... 128/692
4,004,576  1/1977  Gähwiler et al. .................... 128/713

FOREIGN PATENT DOCUMENTS 2942725  5/1981  Fed. Rep. of Germany ...... 128/736

OTHER PUBLICATIONS

R. Wassen and B. Olsson, *A Cardiac Output Computer for Thermal Dilution,* Jan. 1970, pp. 78-80.

Primary Examiner—Kyle L. Howell
Assistant Examiner—Ruth S. Smith
Attorney, Agent, or Firm—Gordon L. Peterson

[57] ABSTRACT

Updated cardiac output measurements are obtained using a reference value of cardiac output and the natural change in phase of variations in blood temperature. The reference value of cardiac output can be obtained using a thermodilution technique. The variations in blood temperature are sensed at appropriate locations, such as in the right atrium and the pulmonary artery. The temperature information is processed to provide a signal which is related to the velocity of the blood, and the signal and the reference value of cardiac output are used to provide the updated cardiac output measurement.

12 Claims, 4 Drawing Figures

APPARATUS AND METHOD FOR MEASURING CARDIAC OUTPUT

BACKGROUND OF THE INVENTION

The measurement of cardiac output, i.e., the total volume of blood pumped by the heart per unit of time provides important information about the effectiveness of the heart as a pump and of blood circulation. Many techniques, such as indicator dilution and ultrasound techniques, have been employed to obtain cardiac output.

Thermodilution is one common form of indicator dilution used to obtain cardiac output. With this technique, a thermodilution catheter is placed in the right heart so that an injection port of the catheter is in the right atrium and a thermistor on the catheter is located downstream in the pulmonary artery. A bolus of cold saline is injected into the right atrium through the injection port where it mixes with the blood and produces a temperature change which is detected by the thermistor. From this, a thermodilution curve can be plotted, and the shape of the curve depends on the flow rate.

One problem with a thermodilution technique that involves the injection of cold saline is that it cannot be carried out continuously. Accordingly, this technique is not suitable for providing continuous cardiac output information.

There is a natural variation in temperature in the blood at certain upstream and downstream locations in the circulatory system. For example, the temperature at upstream locations, such as the inferior vena cava, the superior vena cava and the right atrium, varies as does the temperature downstream in the pulmonary artery. The blood temperature at these locations varies with respiration, and the temperature variations at the upstream locations are out of phase with the variations at the downstream location. By appropriately processing this temperature information, the length of time required for the blood to travel between the upstream and downstream locations and the blood velocity between these two locations can be determined. Although techniques for accomplishing this are known, this velocity information is not usable directly to determine cardiac output because, over a length of time, the volume of the system between the two locations at which the temperapure is measured may vary due to, for example, medication taken by the patient and variations in blood volume.

Ultrasound techniques can be used to obtain continuous cardiac output. However, the ultrasound equipment is expensive and it requires the continuous presence of a skilled technician to assure that the ultrasound equipment provides accurate results.

SUMMARY OF THE INVENTION

This invention solves the problems noted above and provides a method and apparatus for continuously measuring cardiac output. This is accomplished by measuring cardiac output to provide a reference value of cardiac output and using the natural change in phase of variations in blood temperature and the reference value of cardiac output for providing an updated measurement of cardiac output. These temperature variations occur cyclically with respiration when the patient is breathing normally or is being mechanically respirated, and some temperature variation may exist during short periods when the patient is not breathing.

With this invention, the reference value can be measured at widely separated times, such as every hour or every few hours. The natural changes in phase of variations in blood temperature are monitored continuously so that the cardiac output measurement can be updated at short intervals, e.g., one or more times per minute, so that continuous cardiac output information is made available.

With this invention, the reference value of cardiac output can be measured using virtually any conventional technique. Because the monitoring of the natural change in phase of variations in blood temperature requires temperature measuring, a cardiac output technique which requires temperature measurement can advantageously be employed. Thus, thermodilution is one preferred method for obtaining the reference value. Accordingly, cold injection thermodilution, which is unsuited for providing a continuous cardiac output measurement, is, in effect, enabled by this invention to provide a continuous measurement of cardiac output.

To update the cardiac output measurement, the temperature of the blood is sensed at two spaced locations within the circulatory system. Although virtually any two locations which experience this natural change in phase of variations in blood temperature can be used, it is preferred to sense the blood temperature in the right atrium and the pulmonary artery. The blood temperature can also be sensed, for example, in the inferior vena cava or the superior vena cava in lieu of the right atrium.

These temperature measurements can advantageously be made by a catheter having thermistors. The catheter is inserted into the circulatory system so as to place the thermistors at the two locations at which temperature information is desired. This temperature information is processed in a known manner to provide a signal which is related to the velocity of the blood traveling between the two locations. This signal may be related to, for example, the length of time required for the blood to travel between these locations or the velocity of the blood between these two locations. This velocity-related signal is then used with the reference value of cardiac output to provide the updated measurement of cardiac output.

The invention, together with additional features and advantages thereof, may best be understood by reference to the following description taken in connection with the accompanying illustrative drawing.

DESCRIPTION OF THE PREFERRED EMBODIMENT

Figure 1:
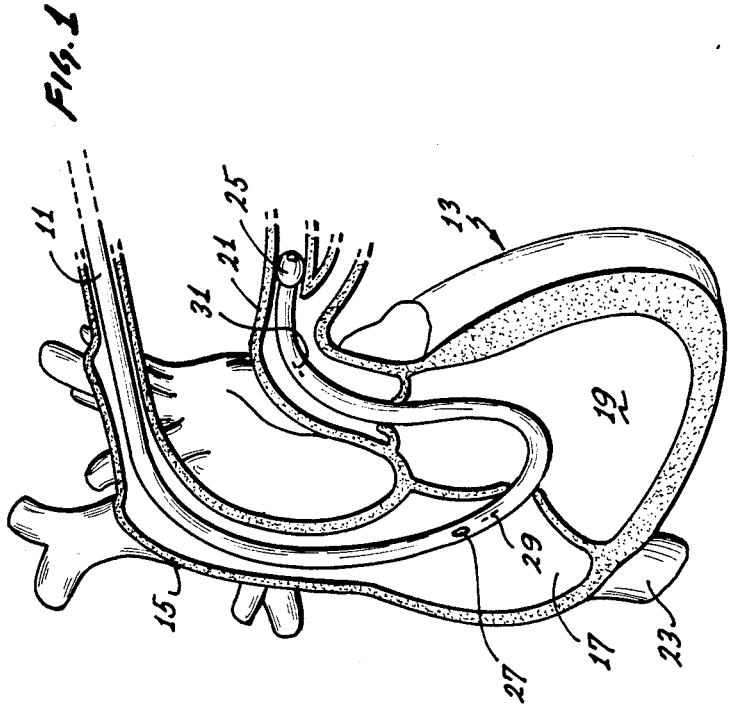
FIG. 1 is a somewhat schematic, perspective, sectional view of a portion of a human heart and a catheter inserted into the heart.

FIG. 1 shows a thermodilution catheter 11 inserted into a human heart 13. More specifically, the catheter 11 is inserted through the superior vena cava 15, the right atrium 17, and the right ventricle 19 into the pulmonary artery 21. The inferior vena cava 23 also leads to the right atrium 17 as shown.

The catheter 11 comprises an inflatable balloon 25 at its distal end, an injection port 27, and temperature sensors in the form of a proximal or upstream thermistor 29 and a distal or downstream thermistor 31. The balloon 25 can be inflated to cause the distal end of the catheter 11 to be drawn through the heart 13 and into the pulmonary artery 21 in accordance with well-known techniques. When so inserted, the injection port 27 and the thermistor 29 lie in the right atrium 17, and the thermistor 31 is in the pulmonary artery 21. As shown in FIG. 1, the thermistor 29 is preferably closely adjacent the injection port 27. If desired, the catheter 11 can be inserted so as to position the thermistor 29 at other locations, such as in the superior vena cava 15 or the inferior vena cava 23. Except for the addition of the thermistor 29, the catheter 11 may be a conventional thermodilution catheter.

The catheter 11 can be used in a conventional manner to inject a bolus of cold saline through the injection port 27 and into the right atrium 17. The cold saline mixes with the blood and produces a temperature change which is detected by the thermistor 31. This temperature change information can be used to plot a thermodilution curve from which the cardiac output can be determined. With this invention, the cardiac output provided by this thermodilution technique constitutes a reference value of cardiac output.

Figure 2:
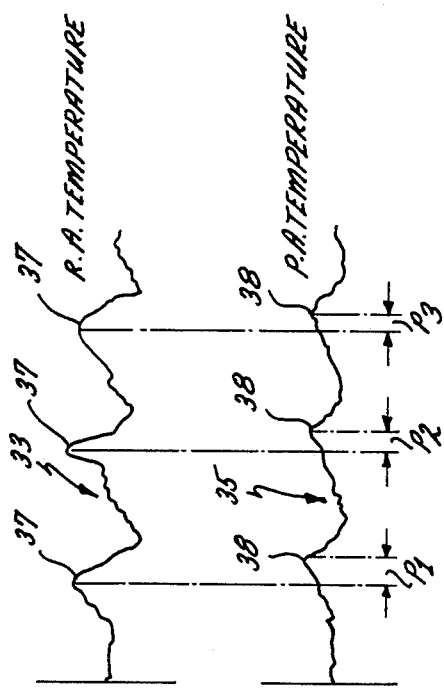
FIG. 2 is a plot of temperature versus time for the blood in the right atrium and the pulmonary artery.

As discussed hereinabove, the temperature of the blood in the right atrium 17 and in the pulmonary artery 21, varies and these temperature variations are out of phase with each other. This can be seen in FIG. 2 where analog temperature signals 33 and 35 show variations of temperature with time in the right atrium and the pulmonary artery, respectively, as sensed by the thermistors 29 and 31. As shown in FIG. 2, the signals 33 and 35 are out of phase, and this is seen most clearly with respect to peaks 37 of the signal 33 which are out of phase with peaks 38 of the signal 35 by different magnitudes $P_1$, $P_2$, $P_3$, etc. The peaks 37 and 38 occur cyclically with respiration when the patient is breathing normally or when the patient is being mechanically respirated. Similar peaks may also exist during short periods when the patient is not breathing.

It is the change in phase of the temperature variations as shown in the signals 33 and 35 as represented, for example, by the differences in the magnitudes $P_1$, $P_2$ and $P_3$, which is used to update the reference value of cardiac output. The signals 33 and 35 can be processed in a known manner to provide a velocity-related signal which is related to the blood velocity between the thermistors 29 and 31 or the length of time required for the blood to travel from the thermistor 29 to the thermistor 31. This information is contained, for example, in a Master of Science thesis entitled, "Characterization of the Thermal Noise in the Pulmonary Artery", by Lindsay A. Weaver, Jr., at the Massachusetts Institute of Technology, September, 1977. Also of interest in this regard is a second Master of Science thesis entitled, "A Technique for Estimation of Cardiac Efficiency Using Thermal Measurements", by Bruce G. Laird, at the Massachusetts Institute of Technology, May 1980.

Figure 3:
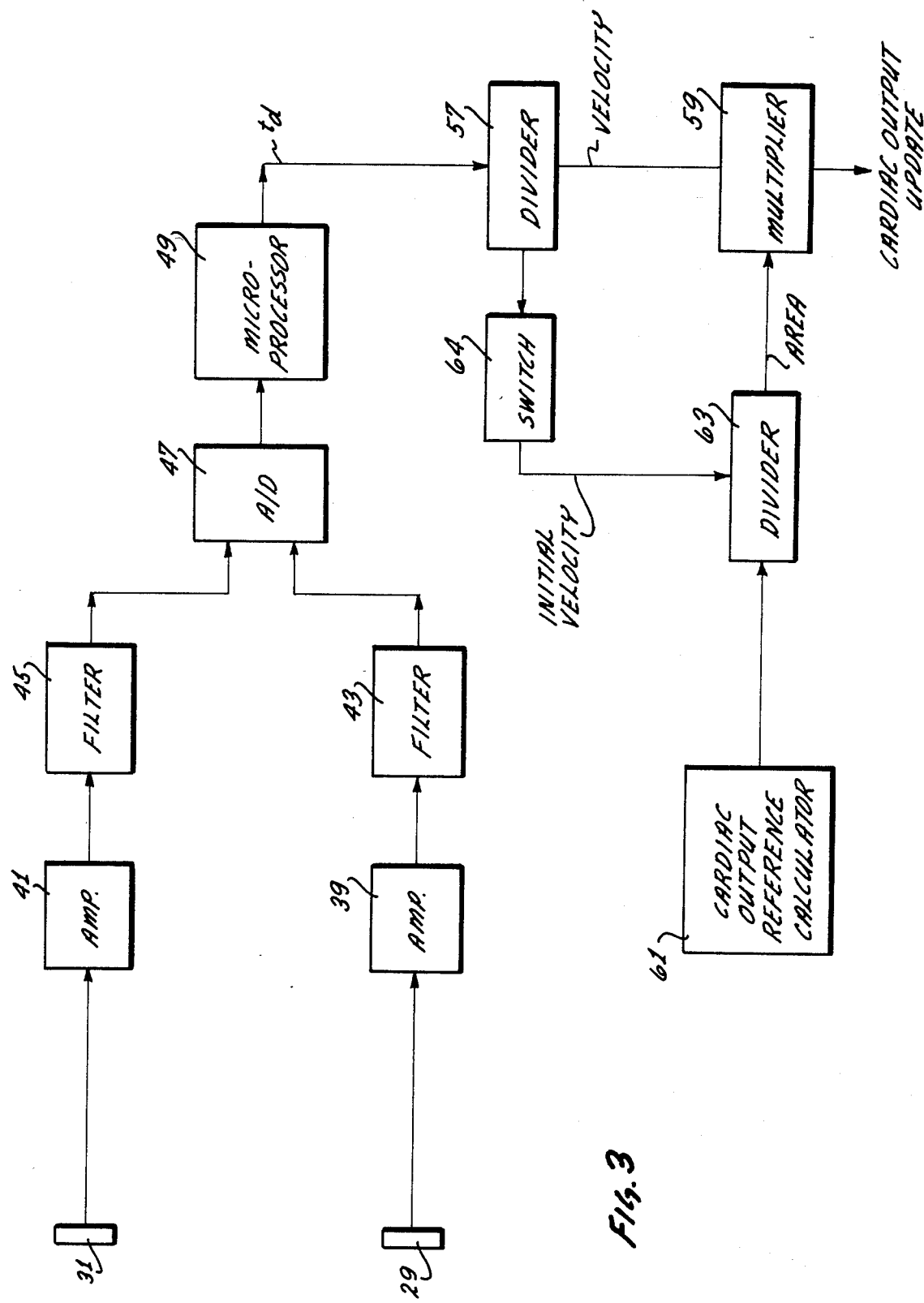
FIG. 3 is a schematic block diagram of an apparatus embodying the principles of this invention.

FIG. 3 shows one way in which the temperature signals 33 and 35 can be processed to provide the velocity-related signal. Each of the temperature signals 33 and 35 from the thermistors 29 and 31 is amplified by isolation amplifiers 39 and 41, respectively and filtered in low-pass filters 43 and 45, respectively. The isolation amplifiers 39 and 41, amplify the associated signal and isolate the patient from potentially dangerous electrical signals. The low-pass filters 43 and 45 eliminate high frequencies and may pass, for example, frequencies up to 20 Hz.

The filtered signals from the filters 43 and 45 are then alternately sampled by an analog-to-digital converter (A/D converter), and the sample values are fed to a microprocessor 49. The sample rate may be, for example, 200 samples per second to thereby provide 100 samples per second of each of the filtered signals.

The microprocessor 49 cross correlates the sample values and determines the length of time required for the blood to flow from the thermistor 29 to the thermistor 31. To accomplish this, the microprocessor 49 implements the following equation:

$$R_{xy}(K) = \frac{1}{N-K} \sum_{i=1}^{N} x(i)y(i-K)$$

where:
$x(i) = x(t_i) =$ sampled value of the signal 33 at the time $t_i$
$y(i) = y(t_i) =$ sampled value of the signal 35 at the time $t_i$
$t_i =$ time of the ith sample
$i =$ index of data samples, $i = 1, 2, \ldots, N$
$N =$ total number of samples of each waveform
$K =$ index of time lag between signals 33 and 35, where K is much less than N.

Figure 4:
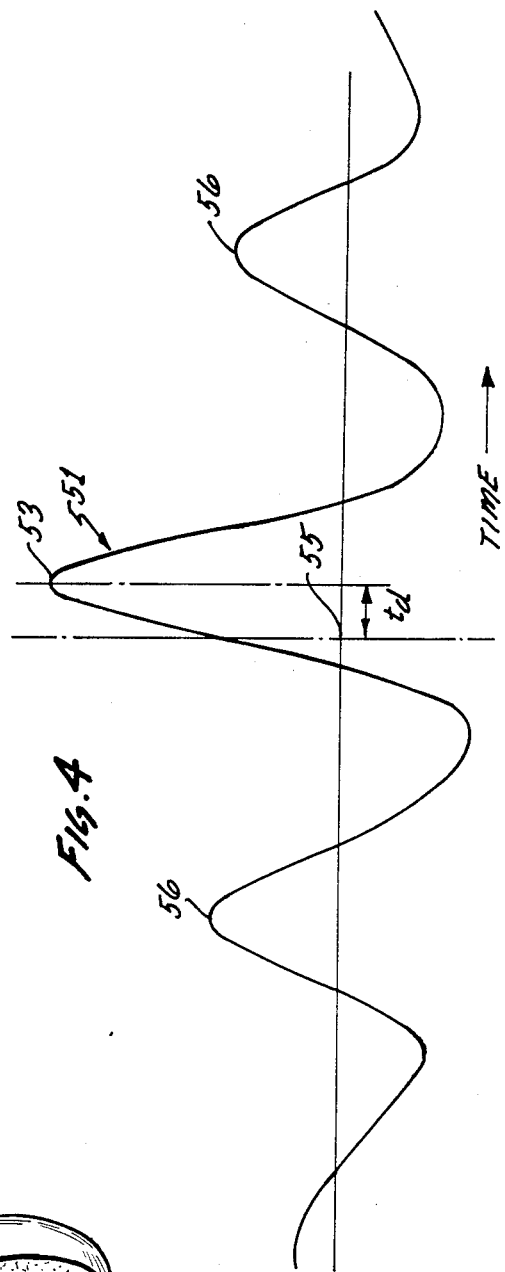
FIG. 4 is a plot of a normalized cross-correlation of the blood temperatures in the right atrium and the pulmonary artery.

The Delay Time $t_d$, i.e., the time for the blood to travel between the thermistors 29 and 31, is obtained by determining the index K corresponding to the maximum value $R_{xy}(K)$ and computing:

Delay Time $= K\Delta t$ where: $\Delta t =$ sampling interval,

The normalized cross correlation of the samples from the A/D converter 47 produces a curve 51 (FIG. 4). The delay time $t_d$ is the time between the maximum peak 53 and the origin 55. The curve 51 also has minor peaks 56 which are a function of patient respiration but which can be ignored for the purposes of determining the length of time for the blood to travel between the thermistors 29 and 31. Because the signal processing techniques to obtain the time $t_d$ are known, they are not described in greater detail herein.

The output of the microprocessor 49 is a velocity-related signal related to the time $t_d$. This signal is applied to a divider 57 which divides the distance between the thermistors 29 and 31 by the time $t_d$ to provide a velocity-related signal which represents the velocity of the blood between the thermistors 29 and 31. This velocity signal is applied to a multiplier 59.

The reference value of cardiac output is calculated in a known manner by a cardiac output reference calculator 61 in response to the injection of the bolus of cold saline through the injection port 27 of the catheter 11 as described above. The reference value of cardiac output is applied to a divider 63. The initially calculated value of velocity from the divider 57 is also applied to the divider 63 through a normally open switch 64 which can be closed manually or automatically following each new calculation of a reference value of cardiac output. The divider 63 divides the reference value of cardiac output in, for example, cubic centimeters per minute, by the initial velocity of the blood between the thermistors 29 and 31 in, for example, centimeters per minute to yield an area signal which is related to cross-sectional area in, for example, square centimeters. This area signal may be stored in a conventional storage circuit 66 and is applied to the multiplier 59 which multiplies it by the velocity signal from the divider 57 in, for example, centimeters per minute to obtain the updated cardiac output in, for example, cubic centimeters per minute. Thus, the reference value of cardiac output from the calculator 61 is updated by a velocity-related signal from the microprocessor 49 which is obtained by processing the temperature signals from the thermistors 29 and 31.

The updated cardiac output measurements using the temperature signals 33 and 35 can be provided as often as desired and may be, for example, once or twice per minute. The divider 63 only receives the first calculated blood velocity from the divider 57 through the normally open switch 64 so that the area input to the multiplier 59 is constant until a new bolus of cold saline is injected through the injection port 27. This enables the calculator 61 to provide a new reference value of cardiac output. With each such new reference value, the divider 63 is provided with the most recently calculated blood velocity from the divider 57 by momentarily closing the switch 64 to enable recalculation of a new area signal for transmission to the multiplier 59.

Although an exemplary embodiment of the invention has been shown and described, many changes, modifications and substitutions may be made by one having ordinary skill in the art without necessarily departing from the spirit and scope of this invention.

I claim:

1. An apparatus for measuring cardiac output using the natural change in phase of variations in blood temperature within the circulatory system, said apparatus comprising:
   means for measuring cardiac output to provide a reference value of cardiac output; and
   means responsive to the natural change in phase of variations in blood temperature within the circulatory system and the reference value of cardiac output for providing an updated measurement of cardiac output.

2. An apparatus as defined in claim 1 wherein said providing means is responsive to said natural change in phase to provide a plurality of updated measurements of cardiac output.

3. An apparatus as defined in claim 1 wherein said providing means includes means for sensing the temperature of the blood at first and second spaced locations within the circulatory system and processing means responsive to the temperature sensed by the sensing means for providing the updated measurement of cardiac output.

4. An apparatus as defined in claim 3 wherein said processing means includes means responsive to the temperature sensed by the sensing means for providing a velocity-related signal which is related to the velocity of the blood traveling between said first and second locations and means responsive to the velocity related signal and the reference value of cardiac output for providing said updated measurement of cardiac output.

5. An apparatus for measuring cardiac output using the natural change in phase of variations in blood temperature which occur at first and second locations within the circulatory system, said apparatus comprising:
   a catheter having first and second temperature sensors adapted to be inserted into the circulatory system so that the temperature sensors can sense the temperature at said first and second locations;
   means for measuring cardiac output to provide a reference value of cardiac output; and
   processing means responsive to the natural change in phase of variations in the blood temperature at the first and second locations as sensed by the temperature sensors and the reference value of cardiac output for providing an updated measurement of cardiac output.

6. An apparatus as defined in claim 5 wherein said catheter includes means for injecting a bolus of liquid into the circulatory system and said measuring means includes means responsive to the temperature change of the liquid for providing the reference value of cardiac output.

7. An apparatus as defined in claim 5 wherein each of said temperature sensors provides an analog temperature signal which is a function of the temperature at the associated location and said processing means includes an analog-to-digital converter for sampling each of said temperature signals and means for cross correlating the values of said samples to provide a velocity-related signal which is related to the velocity of the blood traveling between the first and second locations and means responsive to the velocity related signal and the reference value of cardiac output for providing said updated measurement of cardiac output.

8. A method for measuring cardiac output comprising:
   measuring cardiac output to provide a reference value of cardiac output;
   sensing the temperature of the blood at first and second spaced locations within the circulatory system to provide first and second temperature signals, respectively, said first and second locations being locations at which there is a natural change in phase of variations in blood temperature;
   processing the first and second temperature signals to provide a velocity-related signal which is related to the velocity of the blood traveling between the first and second locations; and
   processing the reference value of cardiac output and the velocity-related signal to provide an updated measurement of cardiac output.

9. A method as defined in claim 8 wherein the first and second locations are within the right atrium and the pulmonary artery, respectively.

10. A method as defined in claim 8 including providing a thermodilution catheter having first and second temperature sensors, said step of sensing includes inserting the catheter into the circulatory system so that the first and second temperature sensors can sense the temperature of the blood in the right atrium and the pulmonary artery, respectively, and said step of measuring the cardiac output to provide a reference value of cardiac output includes injecting a bolus of liquid into the circulatory system upstream of the second temperature sensor.

11. A method as defined in claim 8 wherein said step of measuring the cardiac output is carried out at a first time to provide a first reference value of cardiac output and at a second time to provide a second reference value of cardiac output and said steps of sensing, processing and updating are carried out a plurality of times intermediate said first and second times to provide a plurality of updated measurements of cardiac output.

12. A method as defined in claim 8 wherein said step of sensing includes sensing the temperature of the blood in the pulmonary artery to provide the second temperature signal and in at least one of the inferior vena cava, the superior vena cava and the right atrium to provide the first temperature signal.

* * * * *